United States Patent [19]
Shin et al.

[11] Patent Number: 5,962,267
[45] Date of Patent: Oct. 5, 1999

[54] PROINSULIN DERIVATIVE AND PROCESS FOR PRODUCING HUMAN INSULIN

[75] Inventors: Hang-Cheol Shin, Kwanamyung-shi; Seung-Gu Chang, Seoul; Dae-Young Kim, Bucheon-shi; Chong-Suhl Kim, Taegu, all of Rep. of Korea

[73] Assignee: Hanil Synthetic Fiber Co., Ltd., Rep. of Korea

[21] Appl. No.: 08/600,783

[22] Filed: Feb. 13, 1996

[30] Foreign Application Priority Data

Feb. 15, 1995 [KR] Rep. of Korea .......................... 95-2751

[51] Int. Cl.$^6$ .......................... C12N 15/17; C12N 15/63; C12N 1/21; C07K 14/62
[52] U.S. Cl. .................... 435/69.4; 435/69.7; 435/320.1; 435/325; 435/243; 536/23.4; 536/23.51; 530/303; 530/324
[58] Field of Search ..................................... 530/303, 324; 536/23.1, 23.4; 435/69.4, 69.7, 243, 252.8, 320.1, 325

[56] References Cited

U.S. PATENT DOCUMENTS

| | | | |
|---|---|---|---|
| 4,751,180 | 6/1988 | Cousens et al. ........................ | 435/68 |
| 5,013,653 | 5/1991 | Huston et al. ......................... | 435/69.7 |
| 5,759,807 | 6/1998 | Breece et al. ......................... | 435/69.1 |

OTHER PUBLICATIONS

Powell et al. J. Cell. Biol. 106:1843–1851, 1988.
Chaudhary et al. Nature 339: 394–397, Jun. 1, 1989.
*Insulin: Molecular Biology and Pathology*, ed. Ashcroft, F. M. & Ashcroft, S. J. H., IRL Press, Oxford, 1992.
Markussen, J., *Proc. 1st Intl. Symp. 'Neue Insuline'*, pp. 38–44 (1982), ed. Petersen, et al., Freiburger Greaphische Betriebe.
Chance, R.E., et al., Peptides: Synthesis—Structure—Function, pp. 721–728 (1981), in *Proceedings of the Seventh American Peptide Symposium*, ed. Rich, D. H. & Gross, E., Pierce Chemical Co., Rockford, IL, U.S.A.
Frank, B. H., et al., Peptides: Synthesis—Structure—Function, pp. 729–738 (1981), in *Proceedings of the Seventh American Peptide Symposium*, ed. Rich, D. H. & Gross, E., Pierce Chemical Co., Rockford, IL, U.S.A.
Thim, L., et al., *Proc. Natl. Acad. Sci. U.S.A.*, 83, pp. 6766–6770 (1986).
Markussen, J., et al., *Protein Engineering*, 1, pp. 205–213 (1987).
Stryer, L., *Biochemistry*, 3rd ed., p. 41(1988), Freeman.
Katsoyannis, P. G., et al., *Biochemistry*, 6, pp. 2642–2655(1967).
Steiner, D. F. & Clark, J. L., *Proc. Natl. Acad. Sci. U.S.A.*, 60, pp. 622–629(1968).
Varandani, P. T. & Nafz, M. A., *Arch. Biochem. Biophys.*, 141, pp. 533–537(1970).
Chou, P. Y. & Fasman, G. D., *J. Mol. Biol.*, 115, 134–175(1977).
Dyson, H. J., et al., *J. Mol. Biol.*, 201, 161–200(1988).
Shin, H. C., et al., *Biochemistry*, 32, 6348–6355(1993).
Wright, P. E., et al., *Biochemistry*, 27, 7167–7175(1988).
Zimmerman, S. S. & Scheraga, H. A., *Proc. Natl. Acad. Sci. U.S.A.*, 74(10), 4126–4129(1977).
*Enzymes*, pp. 261–262(1979), ed. Dixon, M. & Webb, E. C., Longman Group Ltd., London.

*Primary Examiner*—Lila Feisee
*Assistant Examiner*—Christine Saoud
*Attorney, Agent, or Firm*—Anderson Kill & Olick

[57] ABSTRACT

A process for preparing human insulin, which comprises the steps of: preparing a DNA encoding a human proinsulin derivative having the following formula (I); inserting the DNA into a vector to construct an expression vector for the expression of the human proinsulin derivative; transforming a host cell with the expression vector; culturing the resulting transformant under a condition that allows the expression of the human proinsulin derivative; purifying human proinsulin derivative from the culture; and preparing human insulin from the human proinsulin derivative by an enzymatic hydrolysis:

B chain-Z-A chain (I)

Wherein, said A and B chains are respectively human insulin chains;

Z is a peptide of formula U-U-X-P-J-(X')n-U-U;

U is an arginine or lysin residue;

X and X' are independently any amino acid residue;

P is a proline residue;

J is a glycine, arginine or lysine residue; and n is 0 or an integer of 1 to 5.

14 Claims, 9 Drawing Sheets

PROINSULIN DERIVATIVE AND PROCESS FOR PRODUCING HUMAN INSULIN

FIELD OF THE INVENTION

The present invention relates to a human proinsulin derivative and a process for producing human insulin by using an expression vector comprising a DNA encoding the human proinsulin derivative. More particularly, it pertains to a human proinsulin derivative which has a short peptide sequence between A and B chains of insulin, in place of the C-peptide; an expression vector comprising a DNA encoding the human proinsulin derivative; a microorganism transformed with the expression vector; and a process for producing human insulin by culturing the microorganism in a suitable medium.

BACKGROUND OF THE INVENTION

Insulin is a polypeptide hormone secreted by the β-cells of pancreas and takes part in regulating the blood sugar level. It consists of two peptide chains, i.e., A and B chains, which are linked by disulfide bridges at their cysteine residues and is produced by a proteolytic processing of proinsulin in pancreatic β-cells(*Insulin: Molecular Biology and Pathology*, ed. Ashcroft, F. M. & Ashcroft, S. J. H., IRL Press, Oxford, 1992). Commercially, human insulin has been produced either by enzymatic process wherein an alanine residue at the 30th position of the B-chain of porcine insulin is replaced with a threonine residue through a transpeptidation reaction using trypsin(Markussen, J., *Proceedings 1st International Symposium 'Neue Insuline'*, pp 38–44(1982), ed. Petersen, K. G., et al., Freiburger Greaphische Betriebe, Freiburg); or, by a process which uses genetically engineered *E. coli*(Chance, R. E., et al., *Peptides: Synthesis-Structure-Function*, pp 721–728(1981), in *Proceedings of the Seventh American Peptide Symposium*, ed. Rich, D. H. & Gross, E., Pierce Chemical Co., Rockford, Ill., U.S.A.; and Frank, B. H., et al., *Peptides: Synthesis-Structure-Function*, pp 729–738(1981), in *Proceedings of the Seventh American Peptide Symposium*, ed. Rich, D. H. & Gross, E., Pierce Chemical Co., Rockford, Ill., U.S.A.) or *Saccharomyces cerevisiae*(Thim, L., et al., *Proc. Natl. Acad. Sci. U.S.A.*, 83, pp 6766–6770(1986); and Markussen, J., et al., *Protein Engineering*, 1, pp 205–213(1987)). As the enzymatic process for producing human insulin from porcine insulin is limited by its high cost, recent studies have been focused on processes for producing human insulin by genetic engineering techniques.

Chance et al. have reported a process for preparing insulin by: producing each of the A and B chains of insulin in the form of a fusion protein by culturing *E. coli* which carries a vector comprising a DNA encoding the fusion protein; cleaving the fusion protein with cyanogen bromide to obtain the A and B chains; sulfonating the A and B chains to obtain sulfonated chains; reacting the sulfonated B chain with an excess amount of the sulfonated A chain; and then, purifying the resultant to obtain insulin(Chance, R. E., et al., supra). However, this process has drawbacks in that it is cumbersome to operate two fermentation processes and the reaction step of the sulfonated A and B chains gives a low yield of insulin, making the process inherently impractical.

Frank et al. have reported a process for preparing insulin, which comprises: producing proinsulin in the form of a fusion protein by culturing *E. coli* which carries a vector comprising a DNA encoding the fusion protein; cutting the fusion protein with cyanogen bromide to obtain proinsulin; sulfonating proinsulin and separating the sulfonated proinsulin; refolding the sulfonated proinsulin to form correct disulfide bonds; treating the refolded proinsulin with trypsin and carboxypeptidase B; and, then, purifying the resultant to obtain insulin(Frank et al., supra). However, the yield of the refolded proinsulin having correct disulfide bonds sharply decreases as the concentration of proinsulin increases. This is due to the misfolding and some degree of polymerization involved and hence the process entails the inconvenience of using laborious purification steps during the recovery of proinsulin.

Thim et al. have reported a process for producing insulin in *Saccharomyces cerevisiae*, which comprises: producing a single chain insulin analogue having a certain amino acid sequence by culturing *Saccharomyces cerevisiae* cells; and isolating insulin therefrom via a series of steps, i.e., purification, enzyme reaction, acid hydrolysis and another purification(Thim, L., et al., supra). This process, although advantageous in that the purification procedures are relatively simple and no refolding procedure is necessary, still gives a low insulin yield, clue to the intrinsically low expression level of yeast system as compared to *E. coli*.

The role of the C-peptide in the folding of proinsulin is not precisely known. One of biochemistry textbooks describes that the C-peptide is necessary for the folding process to occur(*Biochemistry*, 3rd ed., p 41(1988), Freeman), but other studies have shown that about 30 to 50% of correctly folded insulin is obtainable by using the A and B chains alone in the absence of the C-peptide at very low concentration (Katsoyannis, P. G., et al., *Biochemistry*, 6, pp 2642–2655(1967); and Chance, R. E., et al., supra). It has also been shown that a high yield of correctly folded product, comparable to the yield obtainable by using proinsulin, can be obtained by using a peptide wherein the A and B chains are directly joined(Steiner, D. F. & Clark, J. L., *Proc. Natl. Acad. Sci. U.S.A.*, 60, pp 622–629(1968); and Varandani, P. T. & Nafz, M. A., *Arch. Biochem. Biophys.*, 141, pp 533–537(1970)). These results suggest that the role of the C-peptide is simply to bring the A and B chains closely together so as to facilitate the folding process.

According to the known three-dimensional structures of insulins in the Brookhaven Data Bank, the distance between C-terminal α-carbon of B chain(Thr-30) and N-terminal α-carbon of A chain(Gly-1) is roughly 5–11 Å apart, which is a suitable distance for the insertion of a β-turn structure. It has long been recognized that certain amino acid sequences have a high probability of being part of a turn conformation in proteins(Chou, P. Y. & Fasman, G. D., *J. Mol. Biol.*, 115, 135–175(1977)), and this has more recently been shown to be true also for peptides in aqueous solution (Dyson, H. J., et al., *J. Mol. Biol.*, 201, 161–200(1988); and Shin, H. C., et al., *Biochemistry*, 32, 6348–6355(1993)). Proline in the second position and glycine in the third position were found to give the highest β-turn population, and an extensive study revealed that the nature of the amino acid at position 4 influences on the β-turn stability in trans position, and there is a preference for a deprotonated Asp 4 side chain(Wright, P. E., et al., *Biochemistry*, 27, 7167–7175 (1988); and Dyson, H. J., et al., supra).

β-turns are likely sites for the initiation of protein folding, since they are determined by short-range interactions, they limit the conformational space available to the polypeptide chain, and by bringing more distance parts of the polypeptide chain together, they may be instrumental in directing subsequent folding events(Zimmerman, S. S. & Scheraga, H. A., *Proc. Natl. Acad. Sci. U.S.A.*, 74, 4126–4129(1977); and Wright, P. E., et al., supra). These β-turns are also known to play a valuable role in relation to an enzymatic cleavage.

Trypsin is a typical serine protease and hydrolyzes a protein or a peptide at the carboxyl terminal of an arginine or lysine residue(*Enzymes*, pp 261–262(1979), ed. Dixon, M. & Webb, E. C., Longman Group Ltd., London). In particular, facile hydrolysis occurs at a dibasic site where two successive arginine or lysine residues exist, and it is known that hydrolysis occurs most readily where the dibasic site is located in or next to a β-turn structure(Rholam, M., et al., *FEBS Lett.*, 207, 1–6(1986)).

As described above, there exists a need for a high-yield process for producing human insulin in a microorganism, and the present inventors have endeavored to develop an improved insulin production process and succeeded in establishing a new high-yield process by way of using a low molecular weight proinsulin derivative having an easily hydrolyzable β-turn structure.

SUMMARY OF THE INVENTION

Accordingly, it is an object of the present invention to provide a human proinsulin derivative which has a high folding yield and is easily hydrolyzable; and a DNA encoding the same.

Another object of the present invention is to provide an expression vector for the expression of human proinsulin which comprises said DNA.

A further object of the present invention is to provide a microorganism transformed with said expression vector.

Still another object of the present invention is to provide a process for preparing human insulin, which comprises culturing said transformed microorganism in a suitable medium to produce human proinsulin, separating human proinsulin therefrom and producing human insulin from proinsulin.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
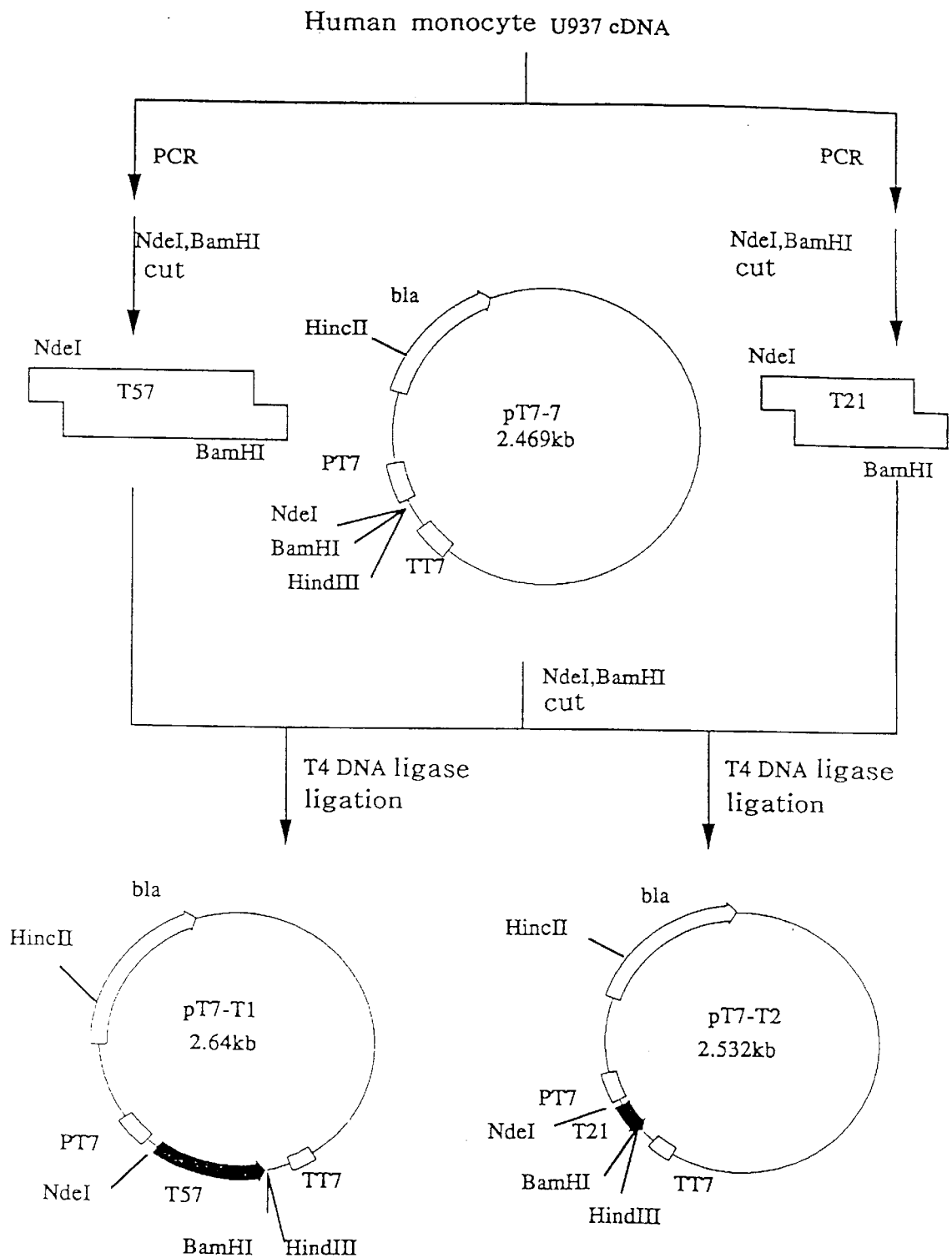
FIG. 1 shows a schematic diagram for preparing plasmids pT7-T1 and pT7-T2.

All references cited herein are hereby incorporated in their entirety by reference.

In accordance with the present invention, there is provided a human proinsulin derivative having formula (I), hereinafter referred to as "miniproinsulin", wherein a peptide, which consists of 12 or Less amino acids and forms a tight β-turn structure, is inserted between A and B chains of human insulin in place of the C-peptide consisting of 35 amino acids:

B chain-Z-A chain          (I)

Wherein, Z is a peptide of formula U-U-X-P-J-(X')n-U-U,
U is an arginine or lysin residue;
X and X' are independently any amino acid residue;
P is a proline residue;
J is a glycine, arginine or lysine residue; and
n is 0 or an integer of 1 to 5.

Preferable miniproinsulins are those wherein X is an alanine, tyrosine, histidine or glycine residue; X' is an aspartic acid, valine, arginine or glycine residue; and n is 0 or 2. Exemplary preferable miniproinsulins are those wherein Z is Arg-Arg-Ala-Pro-Gly-Asp-Val-Lys-Arg(SEQ ID NO: 1); Arg-Arg-Tyr-Pro-Gly-Asp-Val-Lys-Arg(SEQ ID NO: 2); Arg-Arg-His-Pro-Gly-Asp-Val-Lys-Arg(SEQ ID NO: 3); or Arg-Arg-Gly-Pro-Gly-Lys-Arg(SEQ ID NO: 4).

The miniproinsulin of the present invention may be produced as itself or in the form of a fusion protein wherein it is fused with a fusion partner protein, preferably, a β-pleated sheet forming protein.

Exemplary fusion partner proteins which may be employed in the present invention include whole or parts of human tumor necrosis factor(TNF) having an amino acid sequence as shown below(SEQ ID NO: 5); whole or parts of TNF muteins wherein some of the amino acids in SEQ ID NO: 5 are substituted with others; and those polypeptides wherein 1 to 7 amino acids, preferably 7, have been removed from the N-terminal of TNF:

Val Arg Ser Ser Ser Arg Thr Pro Ser Asp Lys Pro Val

Ala His Val Val Ala Asn Pro Gln Ala Glu Gly Gln Leu

Gln Trp Leu Asn Arg Arg Ala Asn Ala Leu Leu Ala Asn

Gly Val Glu Leu Arg Asp Asn Gln Leu Val Val Pro Ser

Glu Gly Leu Tyr Leu Ile Tyr Ser Gln Val Leu Phe Lys

Gly Gln Gly Cys Pro Ser Thr His Val Leu Leu Thr His

Thr Ile Ser Arg Ile Ala Val Ser Tyr Gln Thr Lys Val

Asn Leu Leu Ser Ala Ile Lys Ser Pro Cys Gln Arg Glu

Thr Pro Glu Gly Ala Glu Ala Lys Pro Trp Tyr Glu Pro

Ile Tyr Leu Gly Gly Val Phe Gln Leu Glu Lys Gly Asp

Arg Leu Ser Ala Glu Ile Asn Arg Pro Asp Tyr Leu Asp

Phe Ala Glu Ser Gly Gln Val Tyr Phe Gly Ile Ile Ala

Leu

A DNA encoding human TNF or a TNF mutein may be chemically synthesized by using a DNA synthesizer, or prepared via a polymerase chain reaction("PCR") (Saiki, K. K., et al., *Science*, 230, pp 1350–1354(1985)) by employing human TNF cDNA as a template and chemically synthesized suitable primers.

For example, the DNA encoding the whole or a part of the TNF mutein may be prepared by: obtaining human TNF DNA by PCR of a human monocyte cDNA library prepared from U937 cell line (Clontech, U.S.A.); and carrying out another PCR by employing the TNF DNA as a template and chemically synthesized primers, i.e., a sense primer carrying a recognition site for a restriction enzyme and modified nucleotide sequences at its 5'-end, and an antisense primer carrying a recognition site for a restriction enzyme at its 5'-end.

Miniproinsulin of the present invention may be chemically synthesized by a peptide synthesizer according to a conventional method, or prepared in a microorganism by using a conventional genetic engineering technology.

For the purpose of producing a miniproinsulin in a microorganism, a compatible host cell, e.g., an *E. coli* or *Saccharomyces cerevisiae* cell is transformed with an expression vector containing a DNA encoding the miniproinsulin alone, or a fused DNA encoding a fusion protein consisting of a fusion partner protein and the miniproinsulin; and the transformed cell is cultured under a condition that allows the expression of the miniproinsulin. Then, the miniproinsulin produced is refolded, hydrolyzed by a proteinase, and purified to obtain human insulin.

Accordingly, the present invention provides a process for the preparation of insulin, which comprises the steps of: preparing a DNA encoding a miniproinsulin; inserting the DNA alone or together with a DNA encoding a fusion partner protein into a suitable vector to construct an expression vector for the expression of the miniproinsulin; transforming a host cell with the expression vector; culturing the resulting transformant under a condition that allows the expression of the miniproinsulin; purifying the miniproinsulin from the culture; and preparing insulin from the miniproinsulin.

An expression vector system may be constructed by inserting the DNA encoding the miniproinsulin alone or by successively inserting the DNAs encoding the fusion partner protein and the miniproinsulin, into a vector containing a suitable promoter, e.g., lac, trp, tac, pL, T3, T7, SP6, SV40, and 1(pL/pR); or by ligating the DNA encoding the miniproinsulin or the fusion protein with a DNA comprising one of those promoters and a ribosome binding region, followed by inserting the ligated DNA into a suitable plasmid, e.g., pBR322.

Expression vectors prepared as above can be introduced into a suitable host cell, e.g., *E. coli*, which is selected by considering a number of factors well known in the art, e.g., compatibility with the chosen vector, ease of recovery of the desired polypeptide, polypeptide characteristics, biosafety and costs, in accordance with conventional methods, e.g., the method of Cohen as described in *Proc. Natl. Acad. Sci. U.S.A.*, 69, 2110(1972) to obtain a transformed *E. coli* cell.

Two of such transformants were designated *E. coli* BL21 (DE3+pT1M1PI) and *E. coli* BL21(DE3+pT2M2PI), and deposited on Dec. 29, 1994 with the Korean Culture Center of Microorganism(KCCM)(Address: Department of Food Engineering, College of Eng., Yonsei University, Sodaemun-gu, Seoul 120-749, Korea) with the accession numbers of KCCM-10059 and KCCM-10060, respectively, under the terms of the Budapest Treaty on the International Recognition of the Deposit of Microorganism for the Purpose of Patent Procedure.

The transformed cell is cultured under a condition that allows expression of the miniproinsulin.

The polypeptides produced in a host cell may be isolated and the desired miniproinsulin may be purified therefrom by a combined use of conventional methods, e.g., cell disruption, centrifugation, sulfitolysis, dialysis, treatment with cyanogen bromide, and HPLC.

Specifically, the miniproinsulin produced in *E. coli* in the form of an inclusion body comprising the fusion protein may be purified by the following process.

The cells in the culture are disrupted by employing ultrasonication, and the inclusion bodies comprising the fusion protein are collected by centrifugation. The inclusion bodies are dissolved in a suitable solvent, e.g., 6M guanidine-HCl; the -SH groups of cysteine residues in the protein are converted to $-SSO_3$ groups by sulfitolysis; and the proteins are then precipitated by dialysis or gel filtration chromatography. The precipitated proteins are collected by centrifugation and washed several times with an aqueous solution. The resulting protein is treated with cyanogen bromide and the resultant is purified by HPLC to obtain the miniproinsulin.

Then, the miniproinsulin is treated with β-mercaptoethanol to refold it and the refolded miniproinsulin is treated with trypsin and carboxypeptidase B, preferably in amounts that the weight ratios of trypsin:carboxypeptidase B:miniproinsulin become 1:5:12500, to obtain insulin therefrom.

As described hereinbefore, the present invention has made it possible to improve the yield of human insulin over the prior art by way of expressing a human miniproinsulin, wherein a short peptide is inserted between A and B chains of human insulin in place of the bulky C-peptide in proinsulin. The short peptide consists only of 7 to 12, preferably 9 amino acids, but it is capable of forming a tighter β-turn structure than the C-peptide. Therefore, the processes of refolding and hydrolyzing can be carried out more efficiently with the miniproinsulin than with the proinsulin.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

PCRs in the Examples were carried out in accordance with the conventional PCR method as described in Saiki, K. K., et al., supra.

EXAMPLE 1

Construction of Plasmid pT7-T150

<Step 1> Preparation of TNF DNA

To obtain a TNF DNA, a polymerase chain reaction(PCR) was carried out in accordance with the method of Saiki, K. K., et al. supra by employing a human monocyte cDNA library(Clontech, U.S.A.), which was prepared from U937 cell line as a template and P1 primers having the following nucleotide sequences:

Primer P1 sense primer(SEQ ID NO: 6):

5'-GCCATACATA TGGTCAGATC ATCTTCTCGA ACC-3' antisense primer(SEQ ID NO: 7):

3'-TGAAA CCCTAGTAAC GGGACACTAT TCCTAGGTGT-5'

<Step 2> Preparation of Plasmid pT7-T150 Containing TNF Mutein DNA

To obtain a TNF mutein DNA, a series of PCRs were carried out by employing the TNF DNA prepared in <Step 1> as a template and P2 and P3 primers having the following nucleotide sequences:

Primer P2

(comprising the desired nucleotide substitution)

sense primer(SEQ ID NO: 8):

5'-GTGGTGCCAA TAGAGGGCCT GTTCCTCATC TAC-3' antisense primer(SEQ ID NO: 9):

3'-CAC CACGGTTATC TCCCGGACAA GGAGTAGATG-5'

-continued

Primer P3

(complementary to the 5'- and 3'-ends of the TNF DNA)

sense primer(SEQ ID NO: 10):

5'-ATACATATGC CGAGTGACAA GCCTGTA-3' antisense primer(SEQ ID NO: 11):

3'-A TGAAACCCTA GTAACGGGCC CCTAGGTACA-5'.

Specifically, the first PCR was carried out by employing the TNF DNA prepared in <Step 1> as a template, P2 sense primer and P3 antisense primer, and the second PCR was carried out according to the same procedure as in the first PCR except that P2 antisense primer and P3 sense primer were employed. The resulting two PCR products were mixed together and then annealed.

Then, the TNF mutein DNA was amplified by PCR employing P3 sense primer having a NdeI recognition site at its 5'-end, and P3 antisense primer having SmaI and BamHI recognition sites at its 3'-end. The resulting PCR product, which was named T150, encodes a TNF mutein wherein 7 amino acids were deleted from the N-terminal of TNF, and serine at the 52nd position, tyrosine at the 56th position and leucine at the 157th position of TNF were substituted with isoleucine, phenylalanine and arginine, respectively.

T150 was digested with NdeI and BamHI, and then ligated into the NdeI/BamHI site of a vector, which was prepared by digesting plasmid pT7-7(Department of Biological Chemistry, Harvard Medical School) with NdeI and BamHI, by using T4 DNA ligase. The resulting plasmid was designated pT7-T150.

EXAMPLE 2

Preparation of Plasmid pT7-T1

PCR was carried out by employing the TNF DNA prepared in <Step 1> as a template, P3 sense primer and an antisense primer having the following nucleotide sequence:

Antisense primer (SEQ ID NO:12):

3'-G ACATGGAGTA GATGAGGGCC CCTAGGTACA-5'

The resulting PCR product, which was named T1, encodes a TNF mutein wherein 7 amino acids were deleted from the N-terminal of TNF and serine at the 52nd position and glutamine at the 61st position were substituted with isoleucine and arginine, respectively.

T1 was digested with NdeI and BamHI, and then ligated into the NdeI/BamHI site of a vector, which was prepared by digesting plasmid pT7-7 with NdeI and BamHI, by using T4 DNA ligase. The resulting plasmid was; designated pT7-T1, and the construction process thereof is shown in FIG. 1.

EXAMPLE 3

Construction of Plasmid pT7-T2

A synthetic polynucleotide T2 which encodes a polypeptide comprising the 8th to 12th amino acids of the N-terminal of TNF, as well as ten histidine residues which facilitate the purification thereof, was synthesized. The amino acid sequence encoded in T2 is as follows(SEQ ID NO: 13):

$H_2N$-Pro Ser Asp Lys Pro His His His His His

His His His His Ser Ser-COOH

A PCR was carried out by employing primers T20-I, T20-II and T20-III in the ratio of 10:1:10, to obtain a DNA comprising polynucleotide T2 and having NdeI and BamHI recognition sites at its 5'- and 3'-ends, respectively:

T20-I(sense primer; SEQ ID NO: 14):

5'-TATACATATG CCGAGTGACA AGCCT-3'

T20-II(sense primer; SEQ ID NO: 15):

5'-AGTGACAAGC CTCATCATCA TCATCATCAT CATCATCATC

ACAGCAG-3'

T20-III(antisense primer; SEQ ID NO: 16):

3'-TAGT AGTGTCGTCG CCTAGGTACA-5'

The resulting PCR product was digested with NdeI and BamHI and then ligated with NdeI/BamHI treated plasmid pT7-7, by using T4 DNA ligase. The resulting plasmid was designated pT7-T2, whose construction process is shown in FIG. 1.

EXAMPLE 4

Construction of Plasmid pT150-hPI

<Step 1> Preparation of Human Proinsulin DNA

On the basis of information on the amino acid sequence of human proinsulin(Ullich, A., et al., *Science*, 612–615 (1980)), a synthetic DNA encoding human proinsulin, which has the following nucleotide sequence(SEQ ID NO: 17), was prepared by using the codons highly preferred in *E. coli* in order to increase the expression rate of the DNA:

5'-TTC GTT AAT CAG CAC CTG TGC GGC TCT CAC CTG GTA

GAA GCT CTG TAC CTG GTT TGC GGT GAA CGT GGT TTT

TTC TAC ACC CCG AAA ACC CGT CGC GAG GCT GAA GAC

CTG CAG GTA GGT CAG GTT GAA CTG GGC GGT GGT CCG

GGT GCA GGC TCT CTG CAG CCG TTG GCG CTG GAA GGT

TCC CTG CAG AAA CGT GGC ATC GTT GAA CAA TGC TGT

ACT AGC ATC TGC TCT CTC TAC CAG CTG GAG AAC TAT

TGT AAC-3'

Specifically, oligonucleotides having the following nucleotide sequences for use in the synthesis of proinsulin gene were prepared by using an ABI DNA automatic synthesizer (model 392) employing the solid-phase phosphite synthesis method:

pTA(SEQ ID NO: 18):

3'-GATCATGT CGTAACAAGT TGCTACGGTG CAAAGACGTC

CCTTGGAAG GTCGCGGTTGC CGACGTCTCT-5' pTB(SEQ ID NO: 19):

5'-AAGCTTTTAC TAGTTACAAT AGTTCTCCAG CTGGTAGAGA

GAGCAGATGC TAGTACAGCA TTGTTCAA-3'

9

-continued pTC(SEQ ID NO: 20):

3'-ACGTC CAGAAGTCGG AGCGCTGCCC AAAAGCCCCA

CATCTTTTTT GGTGCAAGTG GCGTTTGGTC-5' pTD(SEQ ID NO: 21):

5'-CAGAGAGCCT GCACCCGGAC CACCGCCCAG TTCAACCTGA

CCTACCTGCA GGTCTTCAGC CTCGC-3' pTE(SEQ ID NO: 22):

5'-CATGTTCGTT AATCAGCACC TGTGCGGCTC TCACCTGGTA

GAAGCTCTGT ACCTGGTTTG CGGTGAAC-3' p31(SEQ ID NO: 23):

5'-GTACCTGGTT TGCGGTGAAC GTGGT-3' p112(SEQ ID NO: 24):

3'-TAAC ATTGATCATT TTCGAAGCAT-5' pBAM(SEQ ID NO: 25):

5'-GCAGGATCCA TGTTCGTTAA T-3' pHIN(SEQ ID NO: 26):

3'-ATAA CATTGATCAT TTTCGAAACG-5' p71(SEQ ID NO: 27):

5'-GGTGCAGGCT CTCTGCAGCC GTTGG-3' p72(SEQ ID NO: 28):

3'-CCGAG AGACGTCGGC AACCGCGACC-5'

A DNA fragment was prepared by PCR employing oligonucleotides pTA and pTB as templates and oligonucleotides p71 and p112 as primers and then designated fragment pAB. Another fragment, designated fragment pCD, was also prepared in accordance with the same procedures by using oligonucleotides pTC and pTD as templates and oligonucleotides p31 and p72 as primers. Equal amounts of fragments pAB and pCD were mixed together and then annealed. A third fragment, designated fragment pABCD, was then prepared by PCR employing said annealed oligonucleotide as a template and oligonucleotides p31 and p112 as primers.

Further, equal amounts of fragment pABCD and oligonucleotide pTE were mixed together and then annealed. A DNA encoding the entire human proinsulin was prepared by PCR employing said annealed oligonucleotide as a template and oligonucleotides pBAM and pHIN as primers.

<Step 2> Construction of Plasmid pT150-hPI

The human proinsulin DNA obtained in <Step 1> was digested with BamHI and HindIII to obtain a double stranded DNA having adhesive ends and containing recognition sites for BamHI and HindIII at its 5'- and 3'-ends, respectively.

Plasmid pT7-T150 prepared in Example 1 was digested with BamHI and HindIII and then ligated with BamHI/HindIII treated human proinsulin DNA obtained above, by using T4 DNA ligase. The resulting plasmid was designated plasmid pT150-hPI.

EXAMPLE 5

Construction of plasmid pT1-hPI

The hPI DNA obtained in <Step 1> of Example 4 was digested with BamHI and HindIII to obtain a double stranded DNA having adhesive ends and containing recognition sites for BamHI and HindIII at its 5'- and 3'-ends, respectively.

Figure 2:
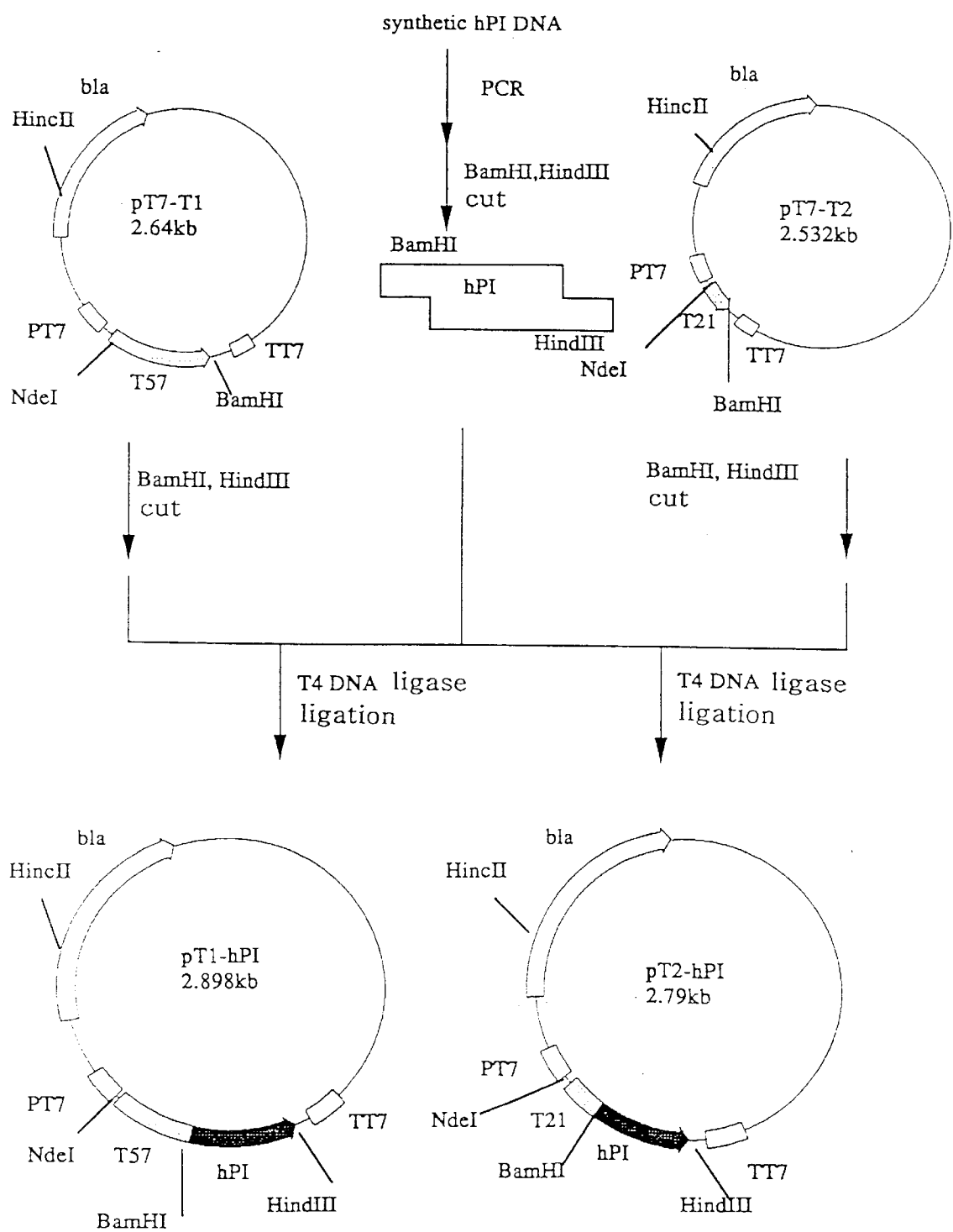
FIG. 2 depicts a schematic diagram for preparing plasmids pT1-hPI and pT2-hPI.

Plasmid pT7-T1 prepared in Example 2 was digested with BamHI and HindIII and then ligated with the BamHI/HindIII-treated hPI DNA obtained above, using T4 DNA ligase. The resulting plasmid was designated pT1-hPI, and the construction process thereof is shown in FIG. 2.

EXAMPLE 6

Construction of Plasmid pT2-hPI

The hPI DNA obtained in <Step 1> of Example 4 was digested with BamHI and HindIII to obtain a double stranded DNA having adhesive ends and containing recognition sites for BamHI and HindIII at its 5'- and 3'-ends, respectively.

Plasmid pT7-T2 prepared in Example 3 was digested with BamHI and HindIII and then ligated with the BamHI/HindIII-treated hPI DNA obtained above, using T4 DNA ligase. The resulting plasmid was designated pT2-hPI, and the construction process thereof is shown in FIG. 2.

EXAMPLE 7

Construction of Plasmid pT1-MiPI

DNAs encoding miniproinsulins, each of which comprises a β-turn forming peptide located between the A and B chains, were prepared in such a way that the 2nd amino acid of said peptide is a proline residue, which is known to induce a tight β-turn structure(Dyson, H. J., et al., *J. Mol. Biol.*, 201, pp 161–200(1988)). Said peptide is Arg-Arg-Ala-Pro-Gly-Asp-Val-Lys-Arg(SEQ ID NO: 1) (M1PI); Arg-Arg-Tyr-Pro-Gly-Asp-Val-Lys-Arg(SEQ ID NO: 2)(M2PI); Arg-Arg-His-Pro-Gly-Asp-Val-Lys-Arg (SEQ ID NO: 3)(M3PI); or Arg-Arg-Gly-Pro-Gly-Lys-Arg(SEQ ID NO: 4)(M4PI).

Specifically, primers having the following nucleotide sequences were prepared by using an automatic DNA synthesizer:

Primer pBAM(SEQ ID NO: 25):

5'-GCAGGATCCA TGTTCGTTAA T-3'

Primer pHIN(SEQ ID NO: 26):

3'-ATAA CATTGATCAT TTTCGAAACG-5'

Primer psM1

Sense Primer(SEQ ID NO: 29)

5'-GCTCCGGGTG ACGTTAAACG TGGCATCGTT GAACAA-3'

Antisense Primer(SEQ ID NO: 30)

3'-TGG GGCTTTTGGG CAGCGCGAGG CCCACTGCAA-5'

Primer psM2

Sense Primer(SEQ ID NO: 31)

5'-TACCCGGGTG ACGTTAAACG TGGCATCGTT GAACAA-3'

Antisense Primer(SEQ ID NO: 32)

3'-TGG GGCTTTTGGG CAGCGATGGG CCCACTGCAA-5'

Primer psM3

-continued

Sense Primer(SEQ ID NO: 33)

5'-CACCCGGGTG ACGTTAAACG TGGCATCGTT GAACAA-3'

Antisense Primer(SEQ ID NO: 34)

3'-TGG GGCTTTTGGG CAGCGGTGGG CCCACTGCAA-5'

Primer psM4

Sense Primer(SEQ ID NO: 35)

5'-GGTCCGGGTA AACGTGGCAT CGTTGAACAA-3'

Antisense Primer(SEQ ID NO: 36)

3'-TGGGGCT TTTGGGCAGC GCCAGGCCCA-5'

A DNA encoding miniproinsulin M1 was prepared as follows. A DNA fragment comprising 5'-end region of miniproinsulin 1("sM1-A") was prepared by PCR employing the proinsulin gene prepared in Example 4 as a template and primer pBAM and antisense primer of psM1. A DNA fragment comprising 3'-end region of miniproinsulin 1("sM1-B") was also prepared by PCR employing the proinsulin gene prepared in Example 4 as a template and primer pHIN and sense primer of psM1. Equal amounts of sM1-A and sM1-B were mixed and annealed. A DNA encoding miniproinsulin M1was prepared by PCR employing said annealed DNA as a template and primers pBAM and pHIN.

The miniproinsulin M1 DNA was digested with BamHI and HindIII to obtain a double stranded DNA having adhesive ends and containing recognition sites for BamHI and HindIII at its 5'- and 3'-ends, respectively.

Plasmid pT7-T1 prepared in Example 2 was digested with BamHI and HindIII and then ligated with BamHI/HindIII treated miniproinsulin M1 DNA obtained above, by using T4 DNA ligase. The resulting plasmid was designated plasmid pT1-M1PI.

Figure 3:
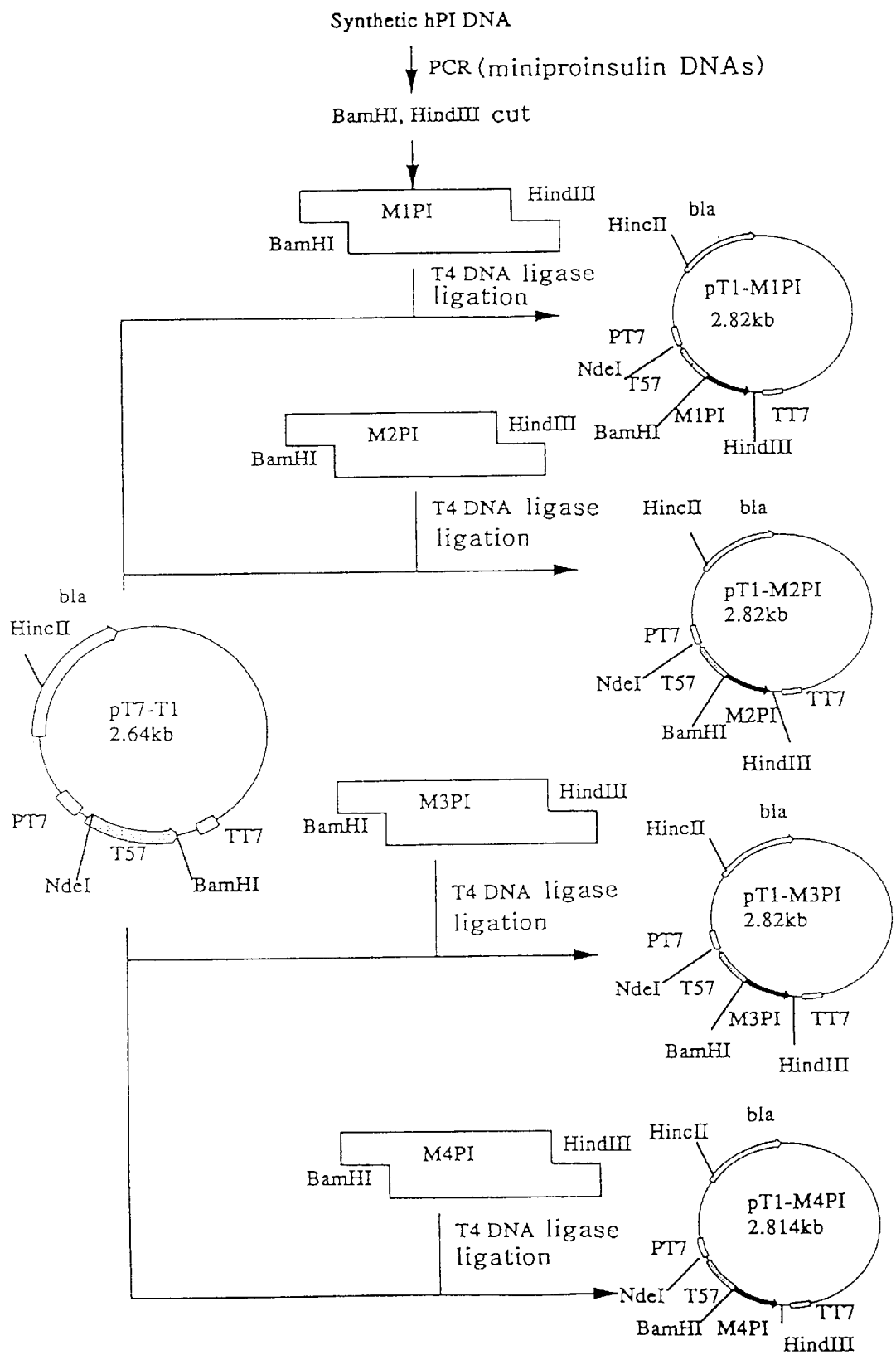
FIG. 3 represents a schematic diagram for preparing plasmids pT1-M1PI, pT1-M2PI, pT1-M3PI and pT1-M4PI.

DNAs encoding miniproinsulin M2, M3 and M4, respectively, were prepared in accordance with the same procedures as above except that each of primers psM2, psM3 and psM4 was used in place of primer psM1, and then, plasmids pT1-M2PI, pT1-M3PI and pT1-M4PI, which comprise miniproinsulin M2, M3 and M4 DNAs, respectively, were also prepared in accordance with the same procedure as above. The construction processes of plasmids pT1-M1PI, pT1-M2PI, pT1-M3PI and pT2-P4PI are shown in FIG. 3.

EXAMPLE 8

Construction of Plasmid pT2-MiPI

Figure 4:
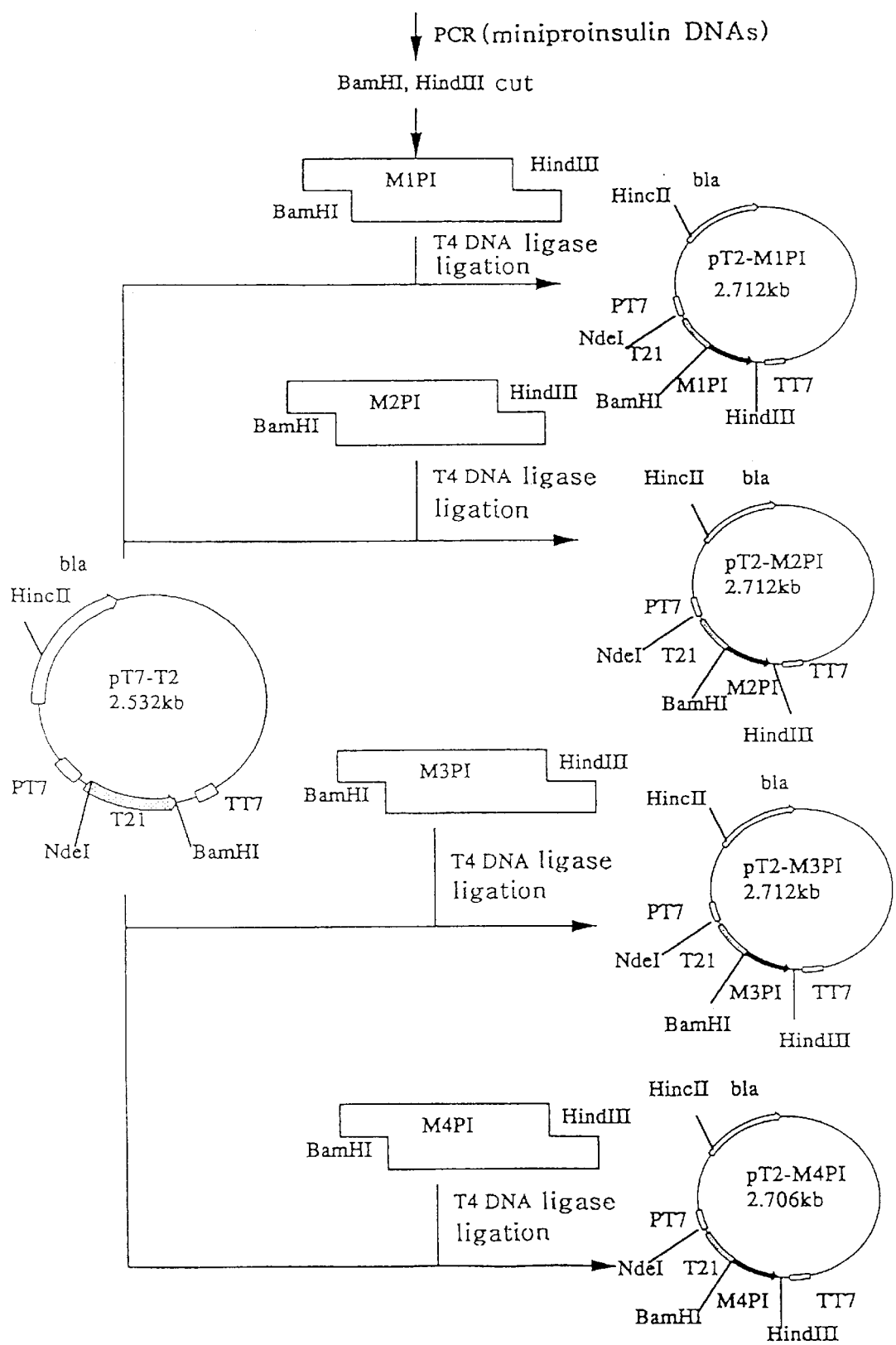
FIG. 4 provides a schematic diagram for preparing plasmids pT2-M1PI, pT2-M2PI, pT2-M3PI and pT2-M4PI.
Figure 5A:
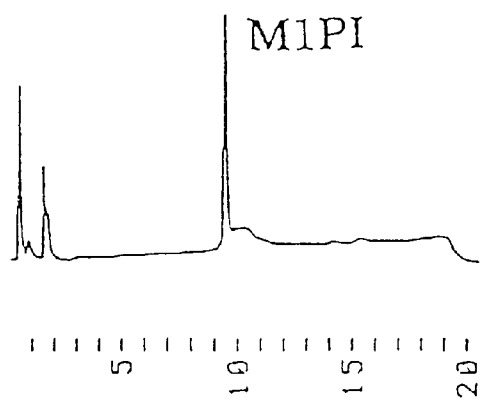
FIGS. 5A to 5E exhibit the HPLC chromatograms of refolded M1PI, M2PI, M3PI, M4PI and hPI, respectively.
Figure 5B:
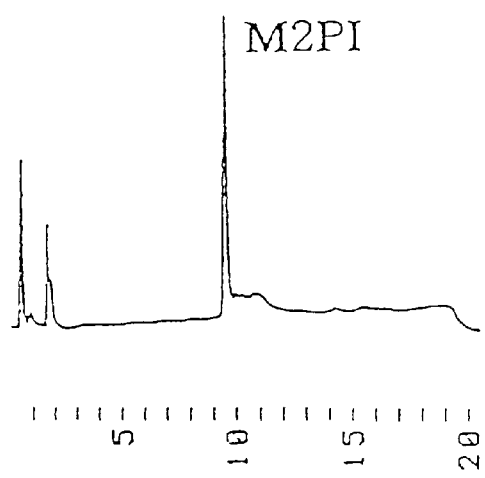
Figure 5C:
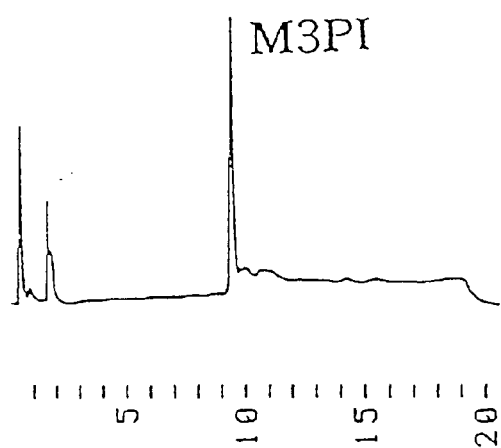
Figure 5D:
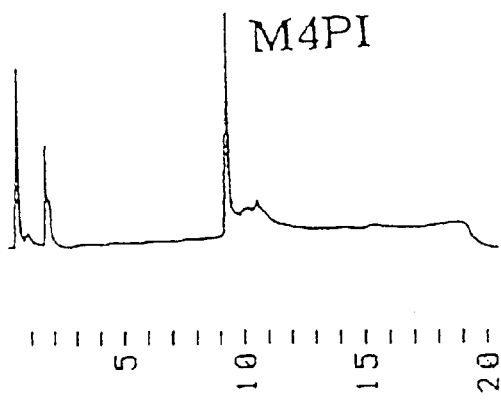
Figure 5E:
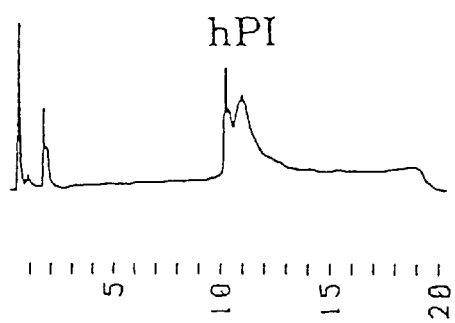
Figure 6A:
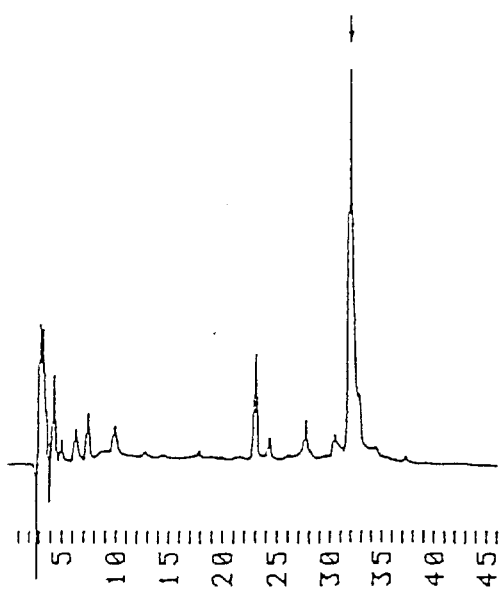
FIGS. 6A to 6E represent the HPLC chromatograms of insulins formed by the hydrolysis of refolded M1PI, M2PI, M3PI, M4PI and hPI respectively.
Figure 6B:
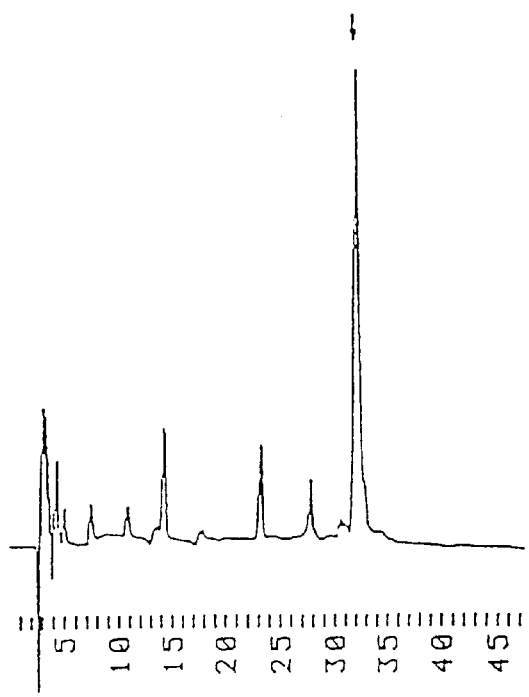
Figure 6C:
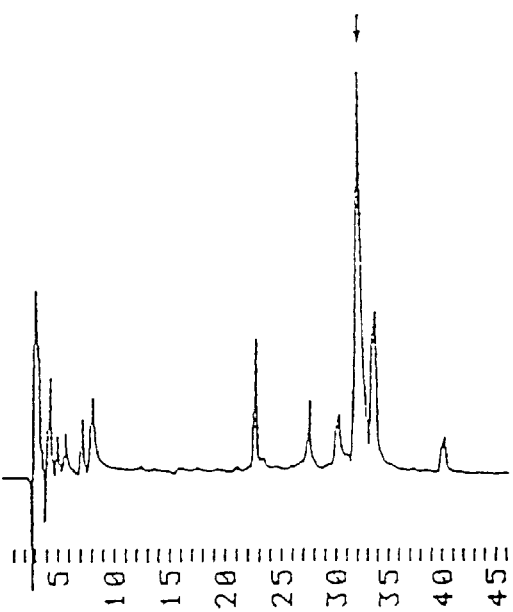
Figure 6D:
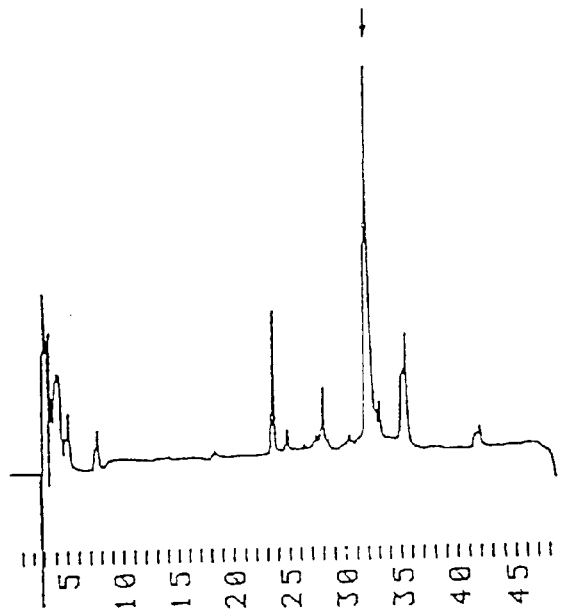
Figure 6E:
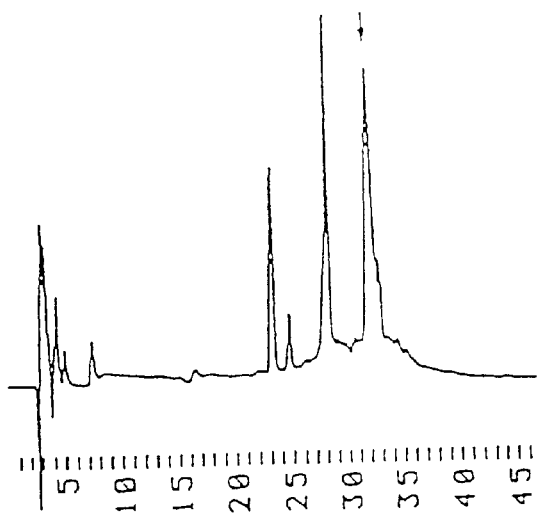

Plasmid pT7-T2 prepared in Example 3 was digested with BamHI and HindIII and then ligated with BamHI/HindIII treated miniproinsulin M1 DNA obtained in Example 7, by using T4 DNA ligase. The resulting plasmid was designated plasmid pT2-M1PI. Plasmids pT2-M2PI, pT2-M3PI and pT2-M4PI, which comprise miniproinsulin M2, M3 and M4 DNAs, respectively, were also prepared in accordance with the same procedures as above. The construction processes of plasmids pT2-M1PI, pT2-M2PI, pT2-M3PI and pT2-M4PI are shown in FIG. 4.

EXAMPLE 9

Expression of TNF-Miniproinsulin Fusion Protein

E. coli XL-1 Blue was transformed with plasmids pT1-M1PI, pT1-M2PI, pT1-M3PI, pT1-M4PI, pT2-M1PI, pT2-M2PI, pT2-M3PI, pT2-M4PI, pT1-hPI and pT2-hPI, respectively, in accordance with the method of Hanahan as described in *DNA Cloning*, vol. 1, Ed. D. M. Glover, IRS Press, 109–135(1985). Thereafter, the ampicillin-resistant colonies formed on the solid medium were selected and then inoculated in 1 ml of LB medium(10 g Bacto tryptone, 5 g Bacto yeast extract and 10 g NaCl per l) containing 50 $\mu$g/ml of ampicillin.

The colonies were incubated at 37° C. for 12 hours and the resulting culture was centrifuged at 8,000×g for 2 min. to obtain *E. coli* cell pellets. Plasmids were separated from the pellets by employing alkaline lysis method(*Methods in Molecular Biology*, Eds. Leonard G. Davis, et al., Elsevier, pp 99–101(1986)) and 1 $\mu$g of the plasmid was dissolved in 50 $\mu$l of TE buffer(pH 8.0). 0.1 $\mu$g of the plasmid solution was mixed with 2 $\mu$l of 10× One-phor-all buffer(100 mM Tris-acetate, 100 mM magnesium acetate, 500 mM potassium acetate), 1 unit of NdeI and 5 units of HindIII, and distilled water was added to the mixture to a final volume of 10 $\mu$l. The solution was reacted at 37° C. for 2 hours and then subjected to 1% agarose gel electrophoresis to confirm the insertion of a DNA fragment.

The plasmids confirmed to comprise the DNA fragment were used to transform the expression host cell *E. coli* BL21(DE3) in accordance with the same procedures as above, and the ampicillin-resistant colonies were selected.

*E. coli* BL21(DE3) cells transformed with plasmids pT1-M1PI and pT2-M2PI, respectively, i.e., *E. coli* BL21(DE3+pT1-M1PI) and *E. coli* BL21(DE3+pT2-M2PI), were deposited at the Korean Culture Center of Microorganisms on Dec. 29, 1994, with the accession numbers of KCCM-10059 and KCCM-10060, respectively.

The colonies selected above were inoculated in 1 ml of LB medium and then cultured at 37° C. for more than 12 hours. The culture was transferred to 50 ml of LB medium containing 50 $\mu$g/ml of ampicillin and, when the O.D. at 600 nm of the culture was 0.1 to 0.4, IPTG(isopropyl thiogalactopyranoside) was added to the culture to a final concentration of 1 mM. The culture was continued at 37° C. for 4 hours with shaking at 200 rpm, and centrifuged at 8,000 rpm for 2 min. to obtain *E. coli* cell pellets.

EXAMPLE 10

Separation and Purification of Miniproinsulin

The *E. coli* cell pellets obtained in Example 8 were suspended in 5 ml of 10 mM sodium phosphate buffer(pH 7.4) and then subjected to ultrasonication to disrupt the cells. The cell lysate was centrifuged at 4° C., 6,000×g for 10 min. to obtain pellets. The pellets were washed with 10-fold volume of 4° C. Triton X-100 buffer(50 mM Tris-HCl, pH 8.0, 10 mM EDTA, 0.5% (v/v) Triton X-100, 100 mM NaCl) and then centrifuged at 8,000×g for 5 min. to separate the pellets. This washing and recovery steps were repeated twice.

The pellets were dissolved in 1 ml of 0.1 M Tris-HCl(pH 8.9) containing 6 M guanidine-HCl, and 50 mg of sodium sulfite and 25 mg of sodium tetrathionate were added to the solution. The resulting mixture was reacted at room temperature for 20 hours and then centrifuged at 12,000×g for 30 min. to obtain a supernatant. The supernatant was placed in a Spectra Por #3 dialysis membrane and then dialyzed against 4° C. distilled water for 24 hours. The resulting dialyzate was centrifuged at 10,000×g for 30 min. to obtain precipitates. To the precipitates were added urea and hydrochloric acid to final concentrations of 8 M and 0.1 M, respectively. 5 mg of cyanogen bromide was then added to the mixture and the resulting solution was reacted at room temperature for 20 hours. The resulting reaction mixture was purified using an HPLC system(Hitachi, Japan) and C-18 reverse-phase column (Pharmacia).

EXAMPLE 11

Refolding of Miniproinsulin and Production of Insulin Therefrom

The sulfonated miniproinsulin obtained in Example 10 was dried, and then dissolved in 50 mM glycine buffer(pH 11.0) to a concentration of 53 $\mu$M. The resulting solution was cooled in ice and 50 mM 2-mercaptoethanol was added thereto to a final concentration of 636 $\mu$M. The mixture was stirred at 4° C. for 19 hours while maintaining the reaction vessel sealed with parafilm. 100 mM phosphoric acid was added to the reaction mixture to stop the reaction and then the products were analyzed at 215 nm with an HPLC. The result is shown in FIGS. 5A to 5E which represent the chromatograms of correctly refolded M1PI, M2PI, M3PI and M4PI, and hPI, respectively. As can be seen from FIGS. 5A to 5E, each of the miniproinsulins of the present invention shows a higher peak area, i.e., a higher yield, than human proinsulin(hPI). The refolding yields of various miniproinsulins and human proinsulin are listed in Table 1.

TABLE 1

| Protein | Refolding Yield (%) |
|---|---|
| M1PI | 59 |
| M2PI | 74 |
| M3PI | 64 |
| M4PI | 53 |
| hPI(proinsulin) | 30 |

Further, 0.5M sodium hydroxide was added to the reaction mixture to pH 7.5 to 8.0. Trypsin and carboxypeptidase were added to the mixture in such amounts that the ratio of trypsin, carboxypeptidase B and miniproinsulin became 1:5:12500. The mixture was reacted at 16° C. for 20 hours and then adjusted to pH 2 to 3 by adding 1M hydrochloric acid to stop the reaction.

The resulting solutions were analyzed at 215 nm with an HPLC. The result is shown in FIGS. 6A to 6E which represent the chromatograms of insulins prepared by treating the refolded M1PI, M2PI, M3PI, M4PI and hPI, respectively, with trypsin and carboxypeptidase B. The result confirms that the miniproinsulins of the present invention give higher yields of insulin than human proinsulin.

What is claimed is:

1. A human proinsulin derivative of formula (I):

B chain-Z-A chain     (I)

wherein:
 said A and B chains are respectively human insulin chains;
 Z is a peptide of formula U-U-X-P-J-(X')n-U-U;
 U is an arginine or lysine residue;
 X is an amino acid residue selected from the group consisting of alanine, tyrosine, histidine and glycine residues;
 X' is an amino acid residue;
 P is a proline residue;
 J is a glycine, arginine or lysine residue; and
 n or 0 or an integer of 1 to 5, with the proviso that, when n is an integer of 1 to 5, X' nearest to the C-terminus is not an arginine or lysine residue.

2. The human proinsulin derivative of claim 1, wherein X is an alanine, tyrosine, histidine or glycine residue; X' is an aspartic acid, valine, arginine or glycine residue; and n is 2.

3. The human proinsulin derivative of claim 1, wherein X is an alanine residue; J is a glycine residue; and (X')n is aspartic acid-valine.

4. The human proinsulin derivative of claim 1, wherein X is a tyrosine residue; J is a glycine residue; and (X')n is aspartic acid-valine.

5. The human proinsulin derivative of claim 1, wherein X is a histidine residue; J is a glycine residue; and (X')n is aspartic acid-valine.

6. The human proinsulin derivative of claim 1, wherein X is a glycine residue; J is an arginine residue; and (X')n is arginine-glycine.

7. The human proinsulin derivative of claim 1, wherein X is a glycine residue; J is a glycine residue; and n is 0.

8. A DNA encoding the human proinsulin derivative of claim 1.

9. An expression vector comprising the DNA of claim 8.

10. The expression vector of claim 9, which is plasmid pT1-M1PI(KCCM-10059) or plasmid pT2-M2PI(KCCM-10060).

11. A microorganism transformed with the vector of claim 9.

12. The microorganism of claim 11, which is *E. coli* BL21(DE3) transformed with plasmid pT1-M1PI(KCCM-10059).

13. The microorganism of claim 11, which is *E. coli* BL21(DE3) transformed with plasmid pT2-M2PI(KCCM-10060).

14. A process for preparing human insulin, which comprises the steps of: preparing a DNA encoding a human proinsulin derivative having formula (I); inserting the DNA into a vector to construct an expression vector for the expression of the human proinsulin derivative; transforming a host cell with the expression vector; culturing the resulting transformant under a condition that allows the expression of the human proinsulin derivative; purifying the human proinsulin derivative from the culture; and preparing human insulin from the human proinsulin derivative by an enzymatic hydrolysis:

$$\text{B chain-Z-A chain} \qquad \text{I}$$

wherein

A and B chains are human insulin chains, respectively;

Z is a peptide of formula U-U-X-P-J-(X')n-U-U;

U is an arginine or lysine residue;

X is an amino acid residue selected from the group consisting of alamine, tyrosine, histidine and glycine residues;

X' is an amino acid residue;

P is a proline residue;

J is a glycine, arginine or lysine residue; and n is 0 or an integer of 1 to 5, with the proviso that when n is an integer from 1 to 5, nearest to the C-terminus is not an arginine or lysine residue.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iii) SEQUENCE DESCRIPTION: SEQ ID NO: 1:

Arg Arg Ala Pro Gly Asp Val Lys Arg
 1               5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iii) SEQUENCE DESCRIPTION: SEQ ID NO: 2:

Arg Arg Tyr Pro Gly Asp Val Lys Arg
 1               5

(2) INFORMATION FOR SEQ ID NO:3:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iii) SEQUENCE DESCRIPTION: SEQ ID NO: 3:

Arg Arg His Pro Gly Asp Val Lys Arg
 1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO: 4:

Arg Arg Gly Pro Gly Lys Arg
 1               5

(2) INFORMATION FOR SEQ ID NO:5:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: protein (iv) SEQUENCE DESCRIPTION: SEQ ID NO: 5:

Val Arg Ser Ser Arg Thr Pro Ser Asp Lys Pro Val Ala His
 1               5                  10                  15

Val Val Ala Asn Pro Gln Ala Glu Gly Gln Leu Gln Trp Leu Asn
                20                  25                  30

Arg Arg Ala Asn Ala Leu Leu Ala Asn Gly Val Glu Leu Arg Asp
                35                  40                  45

Asn Gln Leu Val Val Pro Ser Glu Gly Leu Tyr Leu Ile Tyr Ser
                50                  55                  60

Gln Val Leu Phe Lys Gly Gln Gly Cys Pro Ser Thr His Val Leu
                65                  70                  75

Leu Thr His Thr Ile Ser Arg Ile Ala Val Ser Tyr Gln Thr Lys
                80                  85                  90

Val Asn Leu Leu Ser Ala Ile Lys Ser Pro Cys Gln Arg Glu Thr
                95                  100                 105

Pro Glu Gly Ala Glu Ala Lys Pro Trp Tyr Glu Pro Ile Tyr Leu
                110                 115                 120

Gly Gly Val Phe Gln Leu Glu Lys Gly Asp Arg Leu Ser Ala Glu
                125                 130                 135

Ile Asn Arg Pro Asp Tyr Leu Asp Phe Ala Glu Ser Gly Gln Val
                140                 145                 150

Tyr Phe Gly Ile Ile Ala Leu
                155

(2) INFORMATION FOR SEQ ID NO:6:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 6:

GCCATACATA TGGTCAGATC ATCTTCTCGA ACC                33

(2) INFORMATION FOR SEQ ID NO:7:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 7:

TGTGGATCCT TATCACAGGG CAATGATCCC AAAGT              35

(2) INFORMATION FOR SEQ ID NO:8:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 8:

GTGGTGCCAA TAGAGGGCCT GTTCCTCATC TAC                33

(2) INFORMATION FOR SEQ ID NO:9:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 9:

GTAGATGAGG AACAGGCCCT CTATTGGCAC CAC                33

(2) INFORMATION FOR SEQ ID NO:10:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 10:

ATACATATGC CGAGTGACAA GCCTGTA                       27

(2) INFORMATION FOR SEQ ID NO:11:

(i) SEQUENCE CHARACTERISTICS:
        (A) LENGTH: 31 bases (B) TYPE: nucleic acid
(C) STRANDEDNESS: single
(D) TOPOLOGY: linear (ii) MOLECULE TYPE: primer DNA (iii) ANTI-SENSE: yes (iv) SEQUENCE DESCRIPTION: SEQ ID NO: 11:

ACATGGATCC CCGGGCAATG ATCCCAAAGT A                31

(2) INFORMATION FOR SEQ ID NO:12:

(i) SEQUENCE CHARACTERISTICS:
(A) LENGTH: 31 bases
(B) TYPE: nucleic acid
(C) STRANDEDNESS: single
(D) TOPOLOGY: linear (ii) MOLECULE TYPE: primer DNA (iii) ANTI-SENSE: yes (iv) SEQUENCE DESCRIPTION: SEQ ID NO: 12:

ACATGGATCC CCGGGAGTAG ATGAGGTACA G                31

(2) INFORMATION FOR SEQ ID NO:13:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: protein (iv) SEQUENCE DESCRIPTION: SEQ ID NO: 13:

Pro Ser Asp Lys Pro His His His His His
 1           5                   10

His His His His His Ser Ser
                15

(2) INFORMATION FOR SEQ ID NO:14:

(i) SEQUENCE CHARACTERISTICS:
(A) LENGTH: 25 bases
(B) TYPE: nucleic acid
(C) STRANDEDNESS: single
(D) TOPOLOGY: linear (ii) MOLECULE TYPE: primer DNA (iii) ANTI-SENSE: no (iv) SEQUENCE DESCRIPTION: SEQ ID NO: 14:

TATACATATG CCGAGTGACA AGCCT                       25

(2) INFORMATION FOR SEQ ID NO:15:

(i) SEQUENCE CHARACTERISTICS:
(A) LENGTH: 47 bases
(B) TYPE: nucleic acid
(C) STRANDEDNESS: single
(D) TOPOLOGY: linear (ii) MOLECULE TYPE: primer DNA (iii) ANTI-SENSE: no (iv) SEQUENCE DESCRIPTION: SEQ ID NO: 15:

```
AGTGACAAGC CTCATCATCA TCATCATCAT                                    30

CATCATCATC ACAGCAG                                                   47

(2) INFORMATION FOR SEQ ID NO:16:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 16:

ACATGGATCC GCTGCTGTGA TGAT                                           24

(2) INFORMATION FOR SEQ ID NO:17:

(i) SEQUENCE CHARACTERISTICS:
        (A) LENGTH: 258 bases
        (B) TYPE: nucleic acid
        (C) STRANDEDNESS: single
        (D) TOPOLOGY: linear (ii) MOLECULE TYPE: cDNA to mRNA (iv) SEQUENCE DESCRIPTION: SEQ ID NO: 17:

TTC GTT AAT CAG CAC CTG TGC GGC TCT CAC                              30

CTG GTA GAA GCT CTG TAC CTG GTT TGC GGT                              60

GAA CGT GGT TTT TTC TAC ACC CCG AAA ACC                              90

CGT CGC GAG GCT GAA GAC CTG CAG GTA GGT                             120

CAG GTT GAA CTG GGC GGT GGT CCG GGT GCA                             150

GGC TCT CTG CAG CCG TTG GCG CTG GAA GGT                             180

TCC CTG CAG AAA CGT GGC ATC GTT GAA CAA                             210

TGC TGT ACT AGC ATC TGC TCT CTC TAC CAG                             240

CTG GAG AAC TAT TGT AAC                                             258

(2) INFORMATION FOR SEQ ID NO:18:

(i) SEQUENCE CHARACTERISTICS:
        (A) LENGTH: 68 bases
        (B) TYPE: nucleic acid
        (C) STRANDEDNESS: single
        (D) TOPOLOGY: linear (ii) MOLECULE TYPE: oligonucleotide (iii) ANTI-SENSE: yes (iv) SEQUENCE DESCRIPTION: SEQ ID NO: 18:

TCTCTGCAGC CGTTGGCGCT GGAAGGTTCC CTGCAGAAAC                           40

GTGGCATCGT TGAACAATGC TGTACTAG                                       68

(2) INFORMATION FOR SEQ ID NO:19:

(i) SEQUENCE CHARACTERISTICS:
        (A) LENGTH: 68 bases
        (B) TYPE: nucleic acid
        (C) STRANDEDNESS: single
        (D) TOPOLOGY: linear
```

(ii) MOLECULE TYPE: oligonucleotide (iii) ANTI-SENSE: no (iv) SEQUENCE DESCRIPTION: SEQ ID NO: 19:

AAGCTTTTAC TAGTTACAAT AGTTCTCCAG CTGGTAGAGA          40

GAGCAGATGC TAGTACAGCA TTGTTCAA                       68

(2) INFORMATION FOR SEQ ID NO:20:

(i) SEQUENCE CHARACTERISTICS:
        (A) LENGTH: 65 bases
        (B) TYPE: nucleic acid
        (C) STRANDEDNESS: single
        (D) TOPOLOGY: linear (ii) MOLECULE TYPE: oligonucleotide (iii) ANTI-SENSE: yes (iv) SEQUENCE DESCRIPTION: SEQ ID NO: 20:

CTGGTTTGCG GTGAACGTGG TTTTTTCTAC ACCCCGAAAA          40

CCCGTCGCGA GGCTGAAGAC CTGCA                          65

(2) INFORMATION FOR SEQ ID NO:21:

(i) SEQUENCE CHARACTERISTICS:
        (A) LENGTH: 65 bases
        (B) TYPE: nucleic acid
        (C) STRANDEDNESS: single
        (D) TOPOLOGY: linear (ii) MOLECULE TYPE: oligonucleotide (iii) ANTI-SENSE: no (iv) SEQUENCE DESCRIPTION: SEQ ID NO: 21:

CAGAGAGCCT GCACCCGGAC CACCGCCCAG TTCAACCTGA          40

CCTACCTGCA GGTCTTCAGC CTCGC                          65

(2) INFORMATION FOR SEQ ID NO:22:

(i) SEQUENCE CHARACTERISTICS:
        (A) LENGTH: 68 bases
        (B) TYPE: nucleic acid
        (C) STRANDEDNESS: single
        (D) TOPOLOGY: linear (ii) MOLECULE TYPE: oligonucleotide (iii) ANTI-SENSE: no (iv) SEQUENCE DESCRIPTION: SEQ ID NO: 22:

CATGTTCGTT AATCAGCACC TGTGCGGCTC TCACCTGGTA          40

GAAGCTCTGT ACCTGGTTTG CGGTGAAC                       68

(2) INFORMATION FOR SEQ ID NO:23:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 23:

GTACCTGGTT TGCGGTGAAC GTGGT                                                   25

(2) INFORMATION FOR SEQ ID NO:24:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 24:

TACGAAGCTT TTACTAGTTA CAAT                                                    24

(2) INFORMATION FOR SEQ ID NO:25:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 25:

GCAGGATCCA TGTTCGTTAA T                                                       21

(2) INFORMATION FOR SEQ ID NO:26:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 26:

GCAAAGCTTT TACTAGTTAC AATA                                                    24

(2) INFORMATION FOR SEQ ID NO:27:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 27:

GGTGCAGGCT CTCTGCAGCC GTTGG                                                   25

(2) INFORMATION FOR SEQ ID NO:28:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 28:

CCAGCGCCAA CGGCTGCAGA GAGCC                                    25

(2) INFORMATION FOR SEQ ID NO:29:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 29:

GCTCCGGGTG ACGTTAAACG TGGCATCGTT GAACAA                        36

(2) INFORMATION FOR SEQ ID NO:30:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 30:

AACGTCACCC GGAGCGCGAC GGGTTTTCGG GGT                           33

(2) INFORMATION FOR SEQ ID NO:31:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: primer DNA (iii) ANTI-SENSE: no (iv) SEQUENCE DESCRIPTION: SEQ ID NO: 31:

TACCCGGGTG ACGTTAAACG TGGCATCGTT GAACAA                        36

(2) INFORMATION FOR SEQ ID NO:32:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: primer DNA (iii) ANTI-SENSE: yes (iv) SEQUENCE DESCRIPTION: SEQ ID NO: 32:

AACGTCACCC GGGTAGCGAC GGGTTTTCGG GGT                           33

(2) INFORMATION FOR SEQ ID NO:33:

```
    (i) SEQUENCE CHARACTERISTICS:
         (A) LENGTH: 36 bases
         (B) TYPE: nucleic acid
         (C) STRANDEDNESS: single
         (D) TOPOLOGY: linear (ii) MOLECULE TYPE: primer DNA (iii) ANTI-SENSE: no (iv) SEQUENCE DESCRIPTION: SEQ ID NO: 33:

CACCCGGGTG ACGTTAAACG TGGCATCGTT GAACAA                              36

(2) INFORMATION FOR SEQ ID NO:34:

(i) SEQUENCE CHARACTERISTICS:
         (A) LENGTH: 33 bases
         (B) TYPE: nucleic acid
         (C) STRANDEDNESS: single
         (D) TOPOLOGY: linear (ii) MOLECULE TYPE: primer DNA (iii) ANTI-SENSE: yes (iv) SEQUENCE DESCRIPTION: SEQ ID NO: 34:

AACGTCACCC GGGTGGCGAC GGGTTTTCGG GGT                                 33

(2) INFORMATION FOR SEQ ID NO:35:

(i) SEQUENCE CHARACTERISTICS:
         (A) LENGTH: 30 bases
         (B) TYPE: nucleic acid
         (C) STRANDEDNESS: single
         (D) TOPOLOGY: linear (ii) MOLECULE TYPE: primer DNA (iii) ANTI-SENSE: no (iv) SEQUENCE DESCRIPTION: SEQ ID NO: 35:

GGTCCGGGTA AACGTGGCAT CGTTGAACAA                                     30

(2) INFORMATION FOR SEQ ID NO:36:

(i) SEQUENCE CHARACTERISTICS:
         (A) LENGTH: 27 bases
         (B) TYPE: nucleic acid
         (C) STRANDEDNESS: single
         (D) TOPOLOGY: linear (ii) MOLECULE TYPE: primer DNA (iii) ANTI-SENSE: yes (iv) SEQUENCE DESCRIPTION: SEQ ID NO: 36:

ACCCGGACCG CGACGGGTTT TCGGGGT                                        27
```